(12) United States Patent
Júnior et al.

(10) Patent No.: US 8,835,495 B2
(45) Date of Patent: Sep. 16, 2014

(54) PHARMACEUTICAL COMPOSITION COMPRISING CYCLOBENZAPRINE AND ACECLOFENAC IN ASSOCIATION

(75) Inventors: Dante Alario Júnior, São Paulo (BR); Julio Cesar Gagliardi, São Paulo (BR)

(73) Assignee: Incrementha P, D & I Pesquisa, Desenvolvimento e Inovacao de Farmacos e Medicamentos Ltda, Sao Paulo (BR)

( * ) Notice: Subject to any disclaimer, the term of this patent is extended or adjusted under 35 U.S.C. 154(b) by 912 days.

(21) Appl. No.: 12/227,971

(22) PCT Filed: Jun. 6, 2007

(86) PCT No.: PCT/BR2007/000139
§ 371 (c)(1),
(2), (4) Date: May 14, 2009

(87) PCT Pub. No.: WO2007/140555
PCT Pub. Date: Dec. 13, 2007

(65) Prior Publication Data
US 2009/0306204 A1    Dec. 10, 2009

(30) Foreign Application Priority Data

Jun. 8, 2006 (BR) ..................... 0602179

(51) Int. Cl.
*A01N 37/02* (2006.01)
*A01N 37/06* (2006.01)
*A61K 31/225* (2006.01)
*A01N 33/02* (2006.01)
*A61K 31/135* (2006.01)
*C07C 69/00* (2006.01)
*C07C 211/00* (2006.01)
*A61K 31/216* (2006.01)

(52) U.S. Cl.
CPC ............. *A61K 31/135* (2013.01); *A61K 31/216* (2013.01)
USPC ............ 514/547; 514/656; 564/427; 560/129

(58) Field of Classification Search
CPC ......... A61K 9/28; A61K 9/50; A61K 9/4891; A61K 31/135; A61K 31/216; C07C 13/547; C07C 69/614
USPC .................... 514/547, 656; 560/129; 564/427
See application file for complete search history.

(56) References Cited

U.S. PATENT DOCUMENTS

| 5,842,326 | A | * | 12/1998 | Wolf .............................. 53/425 |
| 6,558,701 | B2 | * | 5/2003 | Bartholomaeus et al. .... 424/472 |
| 6,599,529 | B1 |  | 7/2003 | Skinhøj et al. |
| 2003/0068365 | A1 |  | 4/2003 | Suvanprakorn et al. |

FOREIGN PATENT DOCUMENTS

EP         0009808 A1  *  4/1980

OTHER PUBLICATIONS

Vippagunta et. al., Advanced Drug Delivery Reviews, 2001, Elsevier, vol. 48, pp. 3-26.*
Legrand, Expert Opin. Pharmacother., 2004, Ashley Publ., vol. 5, issue 6, pp. 1347-1357.*
International Search Report from PCT/BR07/00139 (Oct. 9, 2007).

* cited by examiner

*Primary Examiner* — Sarah Pihonak
(74) *Attorney, Agent, or Firm* — Finnegan, Henderson, Farabow, Garrett & Dunner, L.L.P.

(57) ABSTRACT

The present invention relates to an association of active ingredients. More specifically: to an association of cyclobenzaprine and aceclofenac. Additionally, the present invention is also related to the use of aceclofenac and cyclobenzaprine, in association for the preparation of a medicine useful in the treatment of painful muscular diseases, as well as to a method of treatment of painful muscular diseases using an association of aceclofenac and cyclobenzaprine.

3 Claims, No Drawings

PHARMACEUTICAL COMPOSITION COMPRISING CYCLOBENZAPRINE AND ACECLOFENAC IN ASSOCIATION

This application is the U.S. National Phase (§371) Patent Application of International Application No. PCT/BR2007/000139, filed on Jun. 6, 2007, which claims priority to Brazilian Application No. 0602179-4, filed on Jun. 8, 2006, both of which are incorporated herein by reference.

FIELD OF THE INVENTION

The present invention refers to a pharmaceutical composition comprising an association of active ingredients. More specifically: the pharmaceutical composition comprises an association of cyclobenzaprine and aceclofenac. Additionally, the present invention also refers to the use of aceclofenac and cyclobenzaprine in association for preparing a medicine useful in the treatment of painful muscular conditions, as well as a method for treatment of painful muscular conditions using a pharmaceutical composition comprising an association of aceclofenac and cyclobenzaprine.

BACKGROUND OF THE INVENTION

Aceclofenac, also named 2-[2-[2-[(2,6-dichlorophenyl)amino]phenyl]acetyl]oxyacetic acid (CAS RN: 89796-99-6) is a nonsteroidal anti-inflammatory agent, with remarkable anti-inflammatory, analgesic and antipyretic properties. The usual dosage of aceclofenac, normally presented in its acid form, is of two daily doses of 100 mg.

Cyclobenzaprine, also named 3-(5H-dibenzo[a,d]cyclohepten-5-ylidene)-N,N-dimethyl-1-propanamine is a tricyclic muscle relaxant used in the treatment of muscular spasm related with painful musculoskeletal conditions. Usual dosages of cyclobenzaprine (normally presented in the form of hydrochloride salt) are of 3 daily dosages of 5 mg or 10 mg, and the main side effects of the drug are related to drowsiness and dizziness.

Although there are several references about the combined use of cyclobenzaprine with nonsteroidal anti-inflammatory drugs, results of clinical controlled studies are non-conclusive about the real benefit of the use of said association, mainly when the potential side effects of cyclobenzaprine are considered.

Aiming for the obtainment of products with a suitable safety and efficacy profile, as well as easiness of administration for the treatment of diseases which have concomitancy between inflammatory, painful spasm and excessive muscular contraction components, the present inventors noted that association of cyclobenzaprine with aceclofenac can be specially interesting, due to the high analgesic and anti-inflammatory strength of aceclofenac associated to its favorable safety profile, its fast action outset and its prolonged effect.

In a complementary aspect, the present inventors noted that, due to chemical interactions, it is particularly interesting the vehiculation of cyclobenzaprine and aceclofenac in pharmaceutical products that avoid contact between the two active ingredients and/or prevent such interactions.

Within the best knowledge of the present inventors, there is not, in the present state of the art, any publication concerning the efficacy and safety of the specific association of aceclofenac with cyclobenzaprine, neither about the chemical interaction between said active ingredients.

DESCRIPTION OF THE INVENTION

In a first main aspect, the present invention is related to a pharmaceutical composition comprising an association of (i) cyclobenzaprine, its salts or solvates, (ii) aceclofenac, its salts or solvates and, optionally, (iii) one or more excipients pharmaceutically acceptable.

According to the present invention, the term association comprises products in which cyclobenzaprine and aceclofenac are comprised in a single dosage unit (for example, single tablet or capsule), as well as in the form of kits for combined drug vehiculation (for example, blisters comprising aceclofenac tablets and cyclobenzaprine tablets or set of flasks comprising cyclobenzaprine capsules and flasks comprising aceclofenac capsules).

According to the present invention, the term cyclobenzaprine comprises a cyclobenzaprine in the form of free base, as well as salts of cyclobenzaprine with organic or inorganic acids and hydrates or solvates thereof. According to a preferred aspect, cyclobenzaprine is in hydrochloride salt form.

According to the present invention, the term aceclofenac comprises aceclofenac in acid form, as well as salts of aceclofenac with organic or inorganic bases and hydrates or solvates thereof. According to a preferred aspect, aceclofenac is in acid form.

Examples of pharmaceutically acceptable excipients are, for instance, described in the publication: Remington's Pharmaceutical Sciences, $17^{th}$ ed., Mack Publishing Company, Easton, Pa., USA.

In a preferred aspect of the present invention, cyclobenzaprine and aceclofenac are vehicled in pharmaceutical forms and/or products that avoid contact between the two active ingredients.

Examples of pharmaceutical forms that avoid contact between two active ingredients are: triple layer tablets wherein each active ingredient is disposed in a separate layer by an intermediate isolating layer; capsules comprising cyclobenzaprine based granulates and aceclofenac based granulates, separately and preferably coated; capsules comprising cyclobenzaprine based tablets and aceclofenac based tablets, separately and preferably coated.

Examples of pharmaceutical products that avoid contact between the two ingredients are: blisters comprising cyclobenzaprine tablets and aceclofenac tablets, separately; groups of flasks comprising aceclofenac capsules and flasks comprising cyclobenzaprine capsules, separately; cyclobenzaprine and aceclofenac based capsules and/or tablets comprising coated crystals of cyclobenzaprine and/or coated crystals of aceclofenac.

The present invention is not limited by the type or release path of the active ingredients; involving products of immediate, controlled, programmed release, or products of fast disintegration, etc. In the same way, the present invention is not limited by the route of administration of the active ingredients; involving oral, intramuscular, transdermic, intranasal, rectal administration, etc. According to a preferred aspect, the administration route is oral.

The present invention refers to associations of cyclobenzaprine and aceclofenac in pharmaceutically acceptable dosages. According to a preferred aspect, the aceclofenac dosage, in each take, is about 100 mg and preferably cyclobenzaprine dosages in each take are about 2.5 mg to about 10.0 mg.

In a second preferred aspect, the present invention comprises the use of aceclofenac and cyclobenzaprine, together in the preparation of a medicine useful in the treatment of painful muscular diseases.

In a third preferred aspect, the present invention is related to a method for treatment of painful muscular diseases comprising administration of aceclofenac and cyclobenzaprine together.

Examples of painful muscular diseases are: acute and chronic low back pain, cervicalgia, cervicobrachial syndrome, lumbosciatalgia, chronic fatigue syndrome, myofascial pain syndrome, complex regional pain syndrome, polymyalgia rheumatica, polymyositis, dermatomyositis, among others.

According to a preferred aspect, the present invention comprises simultaneously administration of cyclobenzaprine and aceclofenac or administration of cyclobenzaprine and aceclofenac in a time interval less than 60 minutes between the dosages of each drug.

According to a preferred aspect, the present invention still comprises administration of an effective amount of the pharmaceutical composition of the present invention, preferably, in dosages of about 100 mg aceclofenac in each take and dosages of about 2.5 mg to about 10 mg of cyclobenzaprine in each take.

According to another preferred aspect, the present invention comprises a dosage of two daily doses of cyclobenzaprine and two daily doses of aceclofenac.

EXAMPLES

Experimental examples are following described in a detailed manner that illustrates the present invention without limiting its scope:

Example 1

Production of Aceclofenac 100 mg Tablets

Batch size: 3,960 tablets

| Tablet core: | |
|---|---|
| (a) aceclofenac | 396 g |
| (b) microcrystalline cellulose | 356 g |
| (c) sodium croscamelose | 12 g |
| (d) glyceryl stearate palmitate | 8 g |
| (e) Povidone | 24 g |
| (f) Ethyl alcohol | 350 mL |

Sieve in mesh 20 the ingredients (a), (b) and half of the (c) volume. Transfer in a mixer-granulator and mix for 5 minutes.

In a proper recipient, add and dissolve (e) and (f), forming the granulating solution.

Add the granulating solution over the powder formed in the first step, in the mixer-granulator, and proceed to a new mixture until the formation of a wet mass.

Pass the wet mass through mesh 6 and dry in a fluidized bed at 37-40° C.

Calibrate the granulated in 1.0 mm rough mesh.

Sieve the other (c) half in mesh 40, add to the calibrated granulate and mix for 5 minutes.

Sieve (d) in mesh 60, add to the granulate and mix for 3 minutes.

The resulting final mixture was compressed in oblong tablets, with the use of punctures of 11×6.5 mm, with the following characteristics: average weight: 202 mg; dimensions: 11×6.5 mm; hardness: 4.5 to 12.5 kPa; moisture content to 105° C./10 min: maximum of 3%; friability: maximum of 1%.

Coated Tablet Production:

| Coating suspension | |
|---|---|
| (g) Hypromelose/macrogol | 19 g |
| (h) Titanium dioxide | 4 g |
| (i) Polyethylene glycol | 0.8 g |
| (j) Distilled water | 250 mL |

In an suitable vessel containing 200 mL of (j), add (g), under agitation and keep agitation until the solution gets clear (I).

Prepare the suspension of the add pigment, in an suitable vessel, (h) over 50 mL of (j) and homogenize in a shaker for 3 minutes (II).

Mix the solution (I), (II) and (i), with smooth agitation, until the formation of a homogeneous suspension (coating suspension).

Make the application of the coating suspension over the tablet cores, by aspersion, in a coating equipment with air forced circulation.

Average weight of the tablet core: 202 mg; average weight of the coated tablet: 208 mg.

Example 2A

Production of Cyclobenzaprine 2.5 mg Tablets

Batch size: 3,440 tablets

| Tablet core: | |
|---|---|
| (a) cyclobenzaprine hydrochloride | 8.6 g |
| (b) microcrystalline cellulose | 68.8 g |
| (c) tricalcium phosphate | 6.9 g |
| (d) sodium croscamelose | 3.1 g |
| (e) lactose | 100.4 g |
| (f) magnesium stearate | 1.4 g |

Sieve in mesh 20 the ingredients (a), (b), (c), (d) and (e). Transfer for a mixer-granulator and mix for 10 minutes.

Sieve (f) in mesh 60, add to the granulate and mix for 3 minutes.

The resulting final mixture was compressed in oblong tablets, with the use of punctures of 6.5×3.2 mm, with the following characteristics: average weight: 55 mg; dimensions: 6.5×3.2 mm; hardness: 4 to 9.0 kPa; tablet's moisture content in 105° C./10 min: maximum of 6%; friability: maximum of 1%.

Coated Tablet Production:

| Coating suspension | |
|---|---|
| (g) Hypromelose/macrogol | 5.5 g |
| (h) Titanium dioxide | 1.4 g |
| (i) Yellow iron oxide | 0.1 g |
| (j) Distilled water | 250 mL |

In an suitable vessel containing 200 mL of (j), add (g), under agitation and keep agitation until the solution becomes clear (I).

Prepare the suspension of the add pigment, in a suitable vessel, (h) and (i) over 50 mL of (j) and homogenize in a shaker for 3 minutes (II).

Mix (I) and (II) with smooth agitation, until the formation of a homogeneous suspension (coating suspension).

Make the application of the coating suspension over the tablet cores, by aspersion, in a coating equipment with air forced circulation.

Average weight of the tablet core: 55 mg; average weight of the coated tablet: 57 mg.

Example 2B

Production of Cyclobenzaprine 5.0 mg Tablets

Batch size: 3,404 tablets

| Tablet core: | |
| --- | --- |
| (a) cyclobenzaprine hydrochloride | 17.0 g |
| (b) microcrystalline cellulose | 138.2 g |
| (c) tricalcium phosphate | 14.3 g |
| (d) sodium croscamelose | 6.5 g |
| (e) lactose | 195.4 g |
| (f) magnesium stearate | 3.06 g |

The tablet's core was prepared as the example 2A. The final mixture was compressed in oblong tablets, with the use of punctures of 8.5×5 mm, with the following characteristics: average weight: 110 mg; dimensions: 8.5×5 mm; hardness: 5 to 9.0 kPa; tablet's moisture content at 105° C./10 min: maximum of 6%; friability: maximum of 1%.

Coated Tablet Production:

| Coating suspension | |
| --- | --- |
| (g) Hypromelose/macrogol | 9.0 g |
| (h) Titanium dioxide | 2.0 g |
| (i) Yellow iron oxide | 0.2 g |
| (j) Distilled water | 250 mL |

The coating suspension was produced as in Example 2A.

Average weight of the tablet core: 100 mg; average weight of the coated tablet: 113 mg.

Example 2C

Production of Cyclobenzaprine 10.0 mg Tablets

Batch size: 3,333 tablets

| Tablet core: | |
| --- | --- |
| (a) cyclobenzaprine hydrochloride | 33.4 g |
| (b) microcrystalline cellulose | 340 g |
| (c) tricalcium phosphate | 33.3 g |
| (d) sodium croscamelose | 13.3 g |
| (e) lactose | 339.6 g |
| (f) magnesium stearate | 7.0 g |

The tablet's core was prepared as the example 2A. The final mixture was compressed in oblong tablets, with the use of punctures of 12×5.5 mm, with the following characteristics: average weight: 230 mg; dimensions: 12×5.5 mm; hardness: 7 to 10.0 kPa; tablet's moisture content at 105° C./10 min: maximum of 6%; friability: maximum of 1%.

Coated Tablet Production:

| Coating suspension | |
| --- | --- |
| (g) Hypromelose/macrogol | 19.0 g |
| (h) Titanium dioxide | 4.0 g |
| (i) Yellow iron oxide | 0.33 g |
| (j) Distilled water | 250 mL |

The coating suspension was produced as in Example 2A.

Average weight of the tablet core: 230 mg; average weight of the coated tablet: 237 mg.

Example 3

Kit Containing Aceclofenac Tablets and Cyclobenzaprine Tablets in Single Blisters In a PVDC blister with two vesicles are conditioned: one aceclofenac 100 mg tablet (Example 1) and one cyclobenzaprine 5.0 mg tablet (Example 2B). After the closure with an aluminum foil, fourteen of the said blisters are packed in a hard paper cartridge with the instructions to take the blister content in intervals of 12 hours.

Example 4

Kit Containing Aceclofenac Tablets and Cyclobenzaprine Tablets in Cardboards

Two aceclofenac tablets with 100 mg of dosage (Example 1) are conditioned in a blister with two vesicles. Two cyclobenzaprine tablets with 10.0 mg of dosage (Example 2C) are conditioned in a blister with two vesicles. After the closure with aluminum foil, each of the two blisters are then stick to cardboard made of hard paper, with two lines of 4 orifices, aligned in a way to permit blister's mortise, with the formation of two lines of blistered tablets, with the vesicles exposed through the holes; being each of the lines composed by an aceclofenac tablet and a cyclobenzaprine tablet. Five of said cardboards are packed in a hard paper cartridge, along with intake instructions, at intervals of 12 hours, of the content of one line of 2 tablets, composed by one aceclofenac tablet and one cyclobenzaprine tablet.

Example 5

Production of Aceclofenac Granulate

Batch size: 800 g

| Aceclofenac granulate: | |
| --- | --- |
| (a) aceclofenac | 396 g |
| (b) microcrystalline cellulose | 356 g |
| (c) sodium croscamelose | 12 g |
| (d) glyceryl stearate palmitate | 8 g |
| (e) povidone | 24 g |
| (f) ethylic alcohol | 350 mL |

Sieve in mesh 20 the ingredients (a), (b), and half of the (c) volume. Transfer for a mixer-granulator and mix for 5 minutes.

In a proper recipient, add and dissolve (e) and (f), forming the granulating solution.

Add and solubilize (e) in the granulating solution.

Add the granulating solution over the powder formed in the first step, in the mixer-granulator, and proceed to a new mixture until the formation of a wet mass.

Pass the wet mass through mesh 6 and dry in a fluidized bed to 37-40° C.

Calibrate the granulate in 1.0 mm rough mesh.

Sieve the other (c) half in mesh 40, add to the calibrated granulate and mix for 5 minutes.

Sieve (d) in mesh 60, add to the granulate and mix for 3 minutes.

Example 6

Production of Aceclofenac Granulate

Batch size: 767 g

| Tablet core: | |
|---|---|
| (a) cyclobenzaprine hydrochloride | 33.4 g |
| (b) microcrystalline cellulose | 340 g |
| (c) tricalciura phosphate | 33.3 g |
| (d) sodium croscamelose | 13.3 g |
| (e) lactose | 339.6 g |
| (f) magnesium stearate | 7.0 g |

Sieve in mesh 20 the ingredients (a), (b), (c), (d) and (e). Transfer for a mixer-granulator and mix for 10 minutes.

Sieve (f) in mesh 60, add to the granulate and mix for 3 minutes.

Example 7

Production of Capsules Containing One Aceclofenac Based Tablet and One Cyclobenzaprine Based Tablet In a zero size gelatin capsule are conditioned: one aceclofenac tablet with 100 mg dosage (Example 1) and one cyclobenzaprine tablet with 5.0 mg dosage (Example 2B).

Example 8

Comparative Stability Study of Cyclobenzaprine Hydrochloride and Aceclofenac Together and in an Isolate Manner One sample of pure cyclobenzaprine hydrochloride, one sample of pure aceclofenac and one sample of a mixture of cyclobenzaprine hydrochloride and aceclofenac in a ratio of 1 to 1 were disposed in opened glass flasks and were put in an oven with temperature of 50° C. and relative moisture of 90%.

The chromatographic analysis of the samples after a 30 day period showed a significant drop in the content of cyclobenzaprine and aceclofenac in the flask in which the active ingredients were mixed, while the active contents remained unaltered in the flasks that were isolated.

Example 9

Study of Stability of Aceclofenac Coated Tablets (100 mg) and Cyclobenzaprine Hydrochloride Coated Tablets (10 mg)

Aceclofenac coated tablets (Example 1) and 10 mg cyclobenzaprine hydrochloride coated tablets (Example 2C) were encapsulated in gelatin capsules, which where then packaged in glass flasks hermetically closed. The samples were put in an oven at 40° C. and 75% of relative moisture.

After a 60 day period the tablet analysis was made, and it was verified that the content of the actives was practically unaltered.

Example 10

Evaluation of the Safety and Efficacy of the Association of Cyclobenzaprine Hydrochloride and Aceclofenac in Comparison with the Isolated Drugs To evaluate the safety and synergism of the drugs in association in the treatment of acute low back pain in the 7 day period, a multicentric clinical study will be made, phase IIb/III, randomized, double-blind, with 228 assessable patients, conducted under the orientation of qualified physicians.

In the clinical study will be evaluated: (a) the efficacy of the association of cyclobenzaprine hydrochloride and aceclofenac in the treatment of acute lombalgia in comparison with the single drugs; (b) the safety and tolerability of the association of cyclobenzaprine hydrochloride and aceclofenac in the treatment of acute low back pain in comparison with the single drugs; (c) the efficacy and safety of two different doses of cyclobenzaprine hydrochloride (2.5 mg and 5.0 mg) in association with aceclofenac.

For the fulfillment of the clinical study the patients will be selected in accordance with the following criteria: (a) men and women between 18 and 65 years old; (b) back pain narration in the last 5 days, the continuous pain being increased by movement attempts associated with the painful palpation in the back area, with irradiation at maximum to the knees. Will be included both patients that had its first pain episode, as the ones with recurrent pain; and (c) evaluation of the Analogical Visual Scale (AVS) must be ≥60 mm in the basal evaluation; and (d) signature of the term of compliance free and explained by the ethical committee.

The selected patients will be divided in 4 groups that will receive the following treatment: (group 1) aceclofenac 100 mg+cyclobenzaprine hydrochloride 2.5 mg BID; (group 2) aceclofenac 100 mg+cyclobenzaprine hydrochloride 5.0 mg BID; (group 3) aceclofenac 100 mg BID; (group 4) cyclobenzaprine hydrochloride 10 mg BID; Paracetamol 750 will be used in the rescue medicine.

To verify the efficacy the evaluation will be divided in two visits in the $4^{th}$ and $8^{th}$ days.

In the visit made in the $4^{th}$ day will be evaluated: (a) the reduction of pain intensity in relation with the basal (day 1) through AVS; (b) changes in the punctuation of the questionnaire of Roland Morris' life quality in comparison with the basal (day 1).

In the visit made in the $8^{th}$ day, end of treatment, will be evaluated: (a) the intensity's reduction of the pain in comparison to the basal (day 1) through AVS; (b) the number of days for the significant pain remission, defined as punctuation in AVS≤10 mm; (c) change in the punctuation of the questionnaire of Roland Morris' life quality in comparison with the basal (day 1); (d)_ rescue medicine's consumption; (e) patient's global evaluation by the physician; and (f) treatment's global evaluation by the patient itself.

To verify the treatment's safety will be evaluated: (a) the spontaneous narration of adverse events; (b) changes in the punctuation of the questionnaire of Epworth's daytime somnolence in the days 4 and 8 compared with the basal (day 1); and (c) the compliance to the treatment.

It is important to highlight that the present invention is not limited to the description here presented, also contemplating all changes and adaptations that does not apart from the spirit and scope of the invention.

The invention claimed is:

1. A pharmaceutical composition comprising:
   (a) cyclobenzaprine or its salts;
   (b) aceclofenac or its salts; and
   (c) optionally one or more pharmaceutically acceptable excipients;
   wherein said pharmaceutical composition comprises cyclobenzaprine and aceclofenac in a single dosage unit in the form of tablet or hard capsule; and wherein said cyclobenzaprine is not in contact with said aceclofenac.

2. The pharmaceutical composition of claim 1, wherein said tablet is a multilayer tablet in which the layer comprising cyclobenzaprine is physically separated from the layer comprising aceclofenac by an isolating intermediate layer.

3. The pharmaceutical composition of claim 1, wherein said capsule comprises:
   (a) cyclobenzaprine in the form of granules or tablets; and
   (b) aceclofenac in the form of granules or tablets;
   wherein said cyclobenzaprine or aceclofenac granules or tablets are coated.

* * * * *

UNITED STATES PATENT AND TRADEMARK OFFICE
CERTIFICATE OF CORRECTION

PATENT NO.           : 8,835,495 B2
APPLICATION NO.      : 12/227971
DATED                : September 16, 2014
INVENTOR(S)          : Dante Alario Júnior et al.

It is certified that error appears in the above-identified patent and that said Letters Patent is hereby corrected as shown below:

Title page, item (73),

"Assignee:  Incrementha P, D & I Pesquisa, Desenvolvimento e Inovacao de Farmacos e Medicamentos Ltda, Sao Paulo (BR)"

should read

--Assignee:  Incrementha P, D & I Pesquisa, Desenvolvimento e Inovação de Fármacos e Medicamentos Ltda, São Paulo (BR)--.

Signed and Sealed this
Sixteenth Day of December, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,835,495 B2 | Page 1 of 1 |
| APPLICATION NO. | : 12/227971 | |
| DATED | : September 16, 2014 | |
| INVENTOR(S) | : Júnior et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1032 days.

Signed and Sealed this
Twenty-second Day of September, 2015

Michelle K. Lee
*Director of the United States Patent and Trademark Office*